United States Patent

Bowey et al.

Patent Number: 5,616,535
Date of Patent: Apr. 1, 1997

[54] HERBICIDAL COMPOSITIONS INCLUDING GLYPHOSATES AND QUATERNARY AMMONIUM SURFACTANTS

[75] Inventors: Kenneth G. Bowey, Warwickshire, England; Neil A. Baldwin, W. Yorks, United Kingdom

[73] Assignee: Service Chemicals plc., Daventry, United Kingdom

[21] Appl. No.: 426,070

[22] Filed: Apr. 21, 1995

[30] Foreign Application Priority Data

May 20, 1994 [GB] United Kingdom ............... 9410139

[51] Int. Cl.⁶ .......................................... A01N 25/30
[52] U.S. Cl. ............................... 504/206; 71/DIG. 1
[58] Field of Search ............... 504/206; 71/DIG. 1

[56] References Cited

U.S. PATENT DOCUMENTS

| 4,075,002 | 2/1978 | Drewe et al. ......................... 71/92 |
| 5,317,003 | 5/1994 | Kassebaum et al. .................. 504/116 |

FOREIGN PATENT DOCUMENTS

| 0274369 | 12/1990 | European Pat. Off. . |
| 0441764 | 8/1991 | European Pat. Off. . |
| WO921263 | 8/1992 | European Pat. Off. . |
| 0526444 | 3/1993 | European Pat. Off. . |
| 0577914 | 12/1994 | European Pat. Off. . |

*Primary Examiner*—Brian M. Burn
*Attorney, Agent, or Firm*—Wood, Phillips, Van Santen, Clark & Mortimer

[57] ABSTRACT

Herbicidal compositions contain glyphosate (N-phosphonomethylglycine) and a surfactant of formula:

$$\left[ Ar\text{---}(OCH_2CH_2)_{\overline{n}}N\begin{array}{c}R^1\\|\\CH_2\\|\\\text{---}CH_2R^3X^-\\|\\CH_2\\|\\R^2\end{array} \right]$$

in which $R^1$ and $R^2$, are each independently selected from the group consisting of hydrogen and $C_{1-4}$ alkyl; $R^3$ is selected from the group consisting of hydrogen, $C_{-4}$ alkyl and aryl; Ar is an alkyl-substituted aryl system wherein each alkyl substituent contains from 4 to 12 carbon atoms; n is an integer from 1 to 4; and X is a halide, ethylsulphate, methylsulphate, dimethylphosphate, polyalkoxyphosphate, lactate or acetate.

5 Claims, No Drawings

HERBICIDAL COMPOSITIONS INCLUDING GLYPHOSATES AND QUATERNARY AMMONIUM SURFACTANTS

This invention relates to a herbicidal composition which contains glyphosate (N-phosphonomethylglycine).

Glyphosate is a well known herbicide. It has a low solubility in water and is typically formulated as a water soluble salt, such as the mono-isopropylamine (IPA) salt. It is used to kill or control the growth of weeds and other plants. Glyphosate is typically sold commercially as an aqueous concentrate in the form of its IPA salt with one or more surfactants to enhance its uptake.

It has been found that the efficacy of glyphosate formulations can often be further increased by including ammonium sulphate as well as a surfactant. This is described in, for example, Weed Research 1976, 15, 13–19 and 1980, 20, 139–146. Further, EP 0274369 and 0441764 describe glyphosate compositions containing ammonium sulphate and a quaternary ammonium salt surfactant. Improvements in the efficacy of glyphosate have enabled reductions in dose to be achieved.

Despite these improvements in glyphosate compositions, it remains the case that the compositions have a relatively slow speed of activity, and it would be highly advantageous if this could be increased. We have now found that, by using a surfactant chosen from a narrow class of quaternary ammonium compounds not hitherto used or suggested for this purpose, the speed of action of glyphosate (with or without ammonium sulphate) can be significantly improved.

According to the present invention, there is provided a herbicidal composition which comprises a glyphosate compound (by which term we include salts and other herbicidally active derivatives thereof) and a surfactant of the formula:

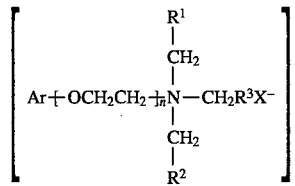

in which $R^1$ and $R^2$, which may be the same or different, are each hydrogen or $C_{1-4}$ alkyl; $R^3$ is hydrogen, $C_{1-4}$ alkyl or aryl; Ar is an alkyl-substituted aryl system wherein the or each alkyl contains from 4 to 12 carbon atoms; n is from 1 to 4; and X is halide, ethylsulphate, methylsulphate, dimethylphosphate, polyalkoxyphosphate, lactate or acetate.

The $C_{1-4}$ alkyl groups include methyl, ethyl, propyl and butyl. The aryl groups include phenyl, naphthalene, anthracene and phenanthrene. The alkyl-substituted aryl system includes groups having one or more aryl members, the or each of which can carry one or more alkyl $C_4$ to $C_{12}$ substituents. Among the $C_4$ to $C_{12}$ alkyl groups are butyl, pentyl, hexyl, heptanyl, octyl, nonyl, decyl, undecyl and dodecyl, including all isomers such as isobutyl etc.

The composition of the invention may, of course, also contain an ammonium salt such as ammonium sulphate or ammonium hydroxide, for example, or other quaternary ammonium compounds such as, for example, DODIGEN 1383 (hexadecyl trimethyl ammonium chloride) and other DODIGEN quaternary ammonium compounds (from Hoechst), REWOQUAT W1599 (quaternary imidazolinium derivative) and other REWOQUAT quaternary ammonium compounds (from Rewo Chemische Werche), QUERTON 16Cl-50 (cetyltrimethyl ammonium chloride) and other QUERTON quaternary ammonium compounds (from Berol Nobel), and BARDAC 2050 (octyldecyl dimethyl ammonium chloride) and other BARDAC and BARQUAT compounds (from Lonza); and ARQUAD 12–50 (dodecyltrimethyl ammonium chloride) and other ARQUAD quaternary ammomium compounds (from Akzo).

The glyphosate can be present as such, but it is preferred to use a salt (or other more readily soluble derivative), the preferred salt being the IPA salt. However, other salts may be used.

Among the preferred compounds of formula I are the diisobutylphenoxyethoxyethyl dimethyl alkaryl ammonium halides, of which the chloride in which the alkaryl group is benzyl is the most preferred. Another preferred compound is diisobutyl cresoxy ethoxy ethyl dimethyl benzyl ammonium chloride. Other compounds which can be used include, for example:

diisobutyl naphthol ethoxy ethyl dimethyl benzyl ammonium chloride diisobutyl anthranol ethyoxy ethyl dimethyl benzyl ammonium chloride diisobutyl phenoxyethoxyethyl dibutyl benzyl ammonium chloride diisobutyl phenoxyethoxyethyl dipentyl benzyl ammonium chloride diisopentyl naphthol ethoxy ethyl dipentyl benzyle ammonium chloride diisopentyl naphthol ethoxy ethyl dipentyl naphthyl ammonium chloride The compositions of the invention can be in any form, i.e. in dry form, or in a liquid concentrate, or in the diluted form ready for application to plants. The relative amounts of glyphosate and surfactant can vary widely, but in general we prefer the ratio of glyphosate to surfactant to be in the range from 50:1 to 1:3 by weight.

As will be understood by those skilled in the art, the invention also includes the use of a quaternary ammonium compound of formula I for forming glyphosate-containing herbicidal compositions. Thus, the quaternary ammonium compound can be used as a tank mix adjuvant. It may be a solid granule wherein the ratio of the amount of glyphosate salt to the amount of quaternary ammonium compound is in the range from 100:1 to 1:3. An ammonium salt may also be included.

The invention further includes the use of a quaternary ammonium compound of formula I and glyphosate, where the glyphosate is present in a concentration of 0.08 to 2% w/v.

In another aspect, the invention also provides the use of an ammonium compound of formula I in conjunction with a linear alcohol ethoxylate (optionally with an ammonium salt) as an adjuvant in a glyphosate spray solution.

The invention further includes a method of controlling plant growth which comprises applying to the plant a herbicidally effective amount of a composition of the invention.

In order that the invention may be more fully understood, the following Examples are given by way of illustration only.

EXAMPLES

An area of turfgrass containing a representative range of annual and perennial grasses, and perennial broad leaf weed species, was treated with various herbicidal compositions. The treatments were applied as foliar sprays in mid-September during a period of cool weather. The herbicidal effects on the turfgrass sward were expressed on a 0–9 visual scale where 0=no effect and 9=complete death of the target plant species. The assessments were made 40, 52 and 96 hours after treatment. The results are set out in the Table.

TABLE

| Composition | Rate of application in litres per hectare | After: | | |
|---|---|---|---|---|
| | | 40 hours | 52 hours | 96 hours |
| None | 0 | 0 | 0 | 0 |
| A | 2 | 0 | 0 | 2 |
| B | 2 | 1 | 1 | 4 |
| C | 1 | 1 | 1 | 3 |
| D | 2 | 0 | 0 | 2 |
| E | 2.5 | 0 | 0 | 1 |
| F | 3 | 0 | 0 | 4 |
| G | 2 | 0 | 1 | 4 |

Composition A was not according to the invention. It consisted of a solution of 480 g/liter glyphosate applied at a rate of 2 liter/ha.

Composition B was according to the invention. It consisted of 2 liters of Composition A to which had been added 1 kg of the following formulation:

| | % w/w |
|---|---|
| Diisobutylphenoxyethoxyethyl dimethyl benzyl ammonium chloride | 5 |
| Ammonium sulphate | 15 |
| Stabiliser (polyethylene glycol PEG 200 or monopropylene glycol) | 3 |
| Water | 77 |

Composition C was according to the invention and was the same as Composition B except that it consisted of 1 liter of Composition A with 1 kg of the formulation defined above.

Composition D was not according to the invention. It consisted of 1 liter of composition A with 1 liter of a mixture of known hydrocarbon surfactants.

Composition E was not according to the invention. It was a known commercially available solution of glyphosate acid (containing 120 g glyphosate acid per liter) applied at the rate of 2.5 liters/hectare.

Composition F was not according to the invention and consisted of 1 liter of composition A with 2 liters of the following solution:

| | w/w |
|---|---|
| Benzylkonium chloride | 10 |
| Ammonium sulphate | 20 |
| Water | 70 |

Composition G was according to the invention and consisted of 1 liter of composition A with 1 liter of a 5% w/w solution in water of diisobutylphenoxyethoxyethyl dimethyl benzyl ammonium chloride.

It can be seen from the Table that glyphosate alone (composition A) shows some effect only at 96 hours after application. In contrast, the compositions of the invention (B, C and G) provide an effect at 40 hours or, when more diluted, at 52 or 96 hours. Further, the effects at 52 and 96 hours are greater than for glyphosate alone, even when the dose rate is much less.

In addition to the above tests, dose response trials were carried out with ammonium sulphate also present in the compositions. The compositions showed similar results to those in the Table, i.e. the compositions containing a surfactant of the invention were much more quickly effective and less active material was required to achieve the same result. The surfactants of the invention have no herbicidal properties of their own: their mode of action is to synergise the glyphosate activity.

Commercially, glyphosate is sold at several different strengths. In particular, formulations are available at 120 g/l, 360 g/l and 480 g/l. The formulation at 480 g/l normally contains a small amount (7% w/w) of tallow amine ethoxylate as the surfactant, and the 360 g/l formulation contains about 17% w/w of the same surfactant. The 120 g/l formulation normally contains a cocoamine ethoxylate with ammonium sulphate and this formulation is alleged to be faster acting than the 360 g/l material. It is clear, however, from the above Table, that formulations of the present invention were faster acting.

The surfactants of the present invention are especially useful with the 480 g/l glyphosate formulations.

We claim:

1. A herbicidal composition comprising a glyphosate compound and a surfactant including a diisobutylphenoxyethoxyethyl dimethyl alkaryl ammonium halide compound.

2. A composition according to claim 1 further comprising an ammonium salt.

3. A composition according to claim 2 wherein the ammonium salt is ammonium sulfate or ammonium hydroxide.

4. A composition according to claim 1 wherein the glyphosate compound is in the form a water soluble salt.

5. The composition according to claim 4 wherein the glyphosate salt composition is a solid granule with the ratio of the glyphosate salt to surfactant being in the range of 100:1 to 1:3, and wherein the composition further includes an ammonium salt as a solid granule in the ratio of 100 parts glyphosate salt to 1 part surfactant and 1 part glyphosate salt to 3 parts surfactant.

* * * * *